United States Patent [19]

Loux et al.

[11] Patent Number: 5,544,276

[45] Date of Patent: Aug. 6, 1996

[54] MINIATURE GAS CHROMATOGRAPH WITH HEATED GAS INLET FITTING, HEATED TUBING, AND HEATED MICROVALVE ASSEMBLY

[75] Inventors: Alan D. Loux, Livermore; R. Sjhon Minners, San Jose; Paul H. Johnson, Oakland, all of Calif.

[73] Assignee: Microsensors Technology, Inc., Fremont, Calif.

[21] Appl. No.: 159,185

[22] Filed: Nov. 30, 1993

[51] Int. Cl.$^6$ .......................... H05B 1/02; G01N 31/08; F24H 1/10
[52] U.S. Cl. .................. 392/480; 392/465; 392/466; 219/201; 73/23.36; 73/23.42; 73/863.11; 96/102; 422/89; 285/41; 137/341
[58] Field of Search .................. 392/480, 482, 392/484, 479, 478, 465–466; 73/23.35, 23.36, 23.42, 863.11, 863.12, 864.12; 96/101–107; 422/89; 285/41; 251/11; 219/201; 137/341

[56] References Cited

U.S. PATENT DOCUMENTS

| | | | |
|---|---|---|---|
| 3,211,169 | 10/1965 | Webb | 137/341 |
| 3,374,660 | 3/1968 | McKinney et al. | 73/23.35 |
| 3,592,046 | 7/1971 | Cramers et al. | 73/23.35 |
| 3,672,226 | 6/1972 | Reid | 73/23.35 |
| 4,004,881 | 1/1977 | Ligon, Jr. | 73/23.35 |
| 4,367,645 | 1/1983 | Fremont | 73/23.35 |
| 4,471,647 | 9/1984 | Jerman et al. | 73/23.35 |
| 4,474,889 | 10/1984 | Terry et al. | |
| 4,650,964 | 3/1987 | Vincent | 392/468 |
| 4,935,040 | 6/1990 | Goedert | 96/101 |
| 5,087,275 | 2/1992 | Pribat et al. | 96/101 |
| 5,150,601 | 9/1992 | Simeroth et al. | 73/863.11 |
| 5,242,471 | 9/1993 | Markhan et al. | 96/105 |
| 5,285,064 | 2/1994 | Willoughby | 73/863.11 |
| 5,325,880 | 7/1994 | Johnson et al. | 251/11 |
| 5,413,139 | 5/1995 | Kusumoto et al. | 137/341 |

FOREIGN PATENT DOCUMENTS

| | | |
|---|---|---|
| 499445 | 8/1992 | European Pat. Off. . |
| 61-288154 | 12/1986 | Japan . |

OTHER PUBLICATIONS

Valco Product Literature, date unknown.
Stephen C. Terry, et al.; "A Gas Chromatographic Air Analyzer Fabricated on a Silicon Wafer"; *IEEE Transactions on Electron Devices*; vol. ED–26, No. 12, Dec. 1979.
Photovac International, "10Splus Digital Gas Chromatograph", Part No. 380200 Rev. B; Copyright 1991.; Index and Chapters 10 and 11.
G. Lee, et al.; "Recent developments in high speed gas chromatography"; *American Library*; Feb. 1989.

*Primary Examiner*—John A. Jeffery
*Attorney, Agent, or Firm*—Skjerven, Morrill, MacPherson, Franklin & Friel; Norman R. Klivans

[57] ABSTRACT

A miniature gas chromatograph with thermostatically-controlled heating of its component parts which contact and conduct the sample to the analytical column. The microvalve assembly of the gas chromatograph is heated by passing a thermostatically-controlled electrical current through a metallic conductor formed on a surface of the microvalve assembly. The tubing which conducts sample from the gas chromatograph sample inlet to the microvalve assembly is heated by passing a thermostatically-controlled electrical current directly through the tubing or through a metal layer formed around the tubing. The sample inlet fitting is heated by a wire heater element wrapped around it. Each heater has an associated temperature sensor for controlling the amount of heating to maintain a predetermined temperature.

10 Claims, 13 Drawing Sheets

MINIATURE GAS CHROMATOGRAPH WITH HEATED GAS INLET FITTING, HEATED TUBING, AND HEATED MICROVALVE ASSEMBLY

BACKGROUND OF THE INVENTION

1. Field of the Invention

This invention relates to gas chromatographs, and more specifically to thermostatic control for a microvalve assembly and associated components of a gas chromatograph or similar instrument.

2. Description of the Prior Art

The gas chromatograph (see U.S. Pat. No. 4,474,889, incorporated by reference) is well-known in the art. A gas chromatograph has three main components: an analytical column which separates physically the components of a sample mixture, a detector to sense the individual components after separation, and an injector to introduce an amount of the sample into the analytical column for separation. Chemicals present in the sample can adhere to components of the gas chromatograph, and thereby degrade or limit the performance of the gas chromatograph.

It is known in the art to heat the analytical column to prevent the chemicals from adhering. It is known in the art to heat the other components of the gas chromatograph system to prevent the adhesion of chemicals therein. Problematically, these other methods are indirect, utilize bulky heating elements and hence consume large amounts of power. For a portable or battery-operated gas chromatograph, less bulky and energy efficient heaters are especially desirable.

Therefore, there is a need for compact, energy-efficient, battery-operable heating for gas chromatograph components to prevent chemicals in the sample from adhering undesirably to the components.

SUMMARY OF THE INVENTION

In accordance with the present invention, the temperature of the internal components of a miniature gas chromatograph which contact the sample and conduct the sample to the analytical column is thermostatically controlled. Each section of the gas chromatograph which has a designated temperature control means is a "heated-zone".

In accordance with the invention, the temperature of the injector tubing and valves (the microvalve assembly) which conduct sample and other fluids in the gas chromatograph is thermostatically controlled. The microvalve assembly is electrically heated and its temperature is sensed, to control the microvalve assembly temperature; the gas chromatograph sample inlet fitting is electrically heated and its temperature is sensed, to control of the sample inlet fitting temperature; electrical current is passed through the tubing that conducts sample from the inlet fitting to the microvalve assembly (the "sample inlet tubing"), or passed through a metal sheath surrounding the tubing, and the temperature of the tubing is sensed, to control the temperature of the tubing; and electronic or electrical circuitry provides the appropriate amount of electrical current to each of the electrical heaters so that the temperature of each heated zone is thermostatically controlled.

The low thermal mass of the system permits rapid heating while consuming little power (allowing battery power). The heating is highly efficient in applying the heat directly to the system components or by physically incorporating the heating elements in the components.

DETAILED DESCRIPTION OF THE INVENTION

Figure 1:
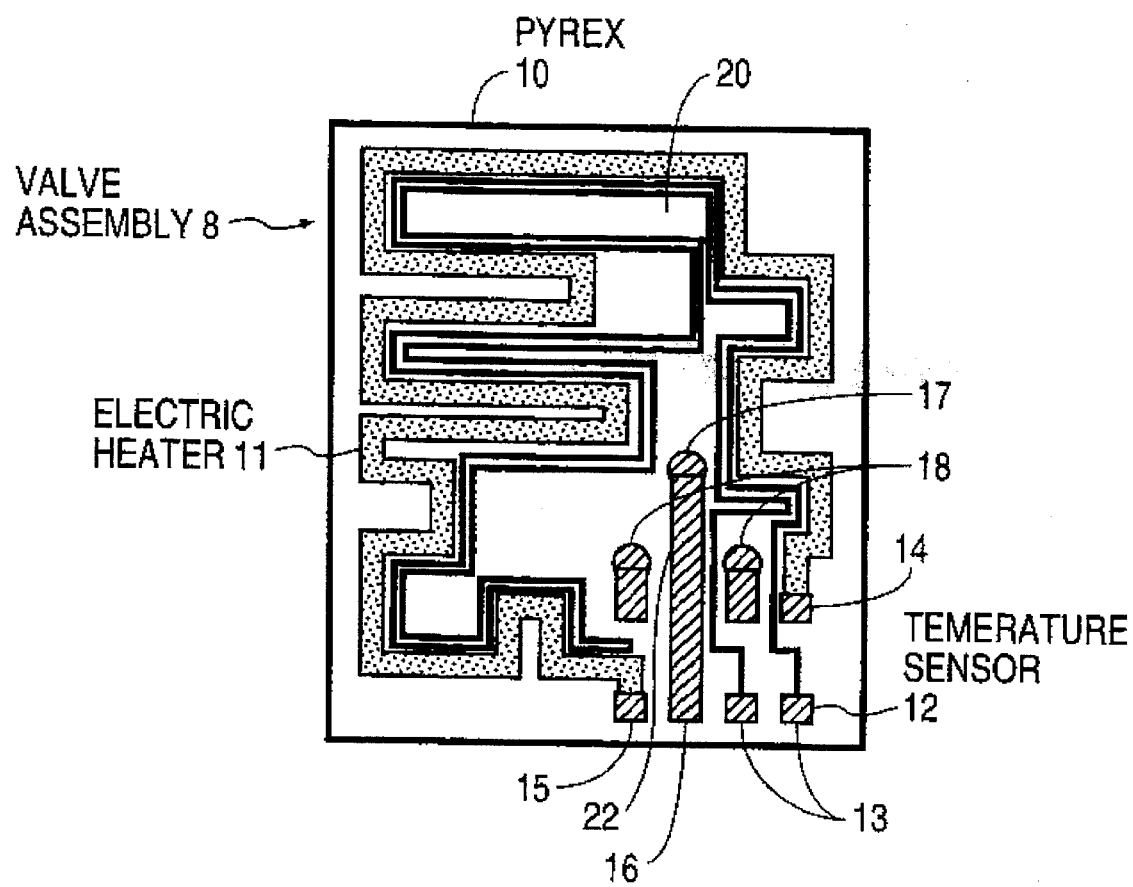
FIG. 1 is a diagram of one embodiment of a microvalve assembly temperature sensor and heater (showing the sensor and heater) traces located on the exterior of the microvalve assembly.

FIG. 1 is a diagram of an embodiment of the temperature sensor and heater heated zone subassembly, which are nickel traces and gold traces which form the heater trace 11 and temperature sensor trace 12 and are located on the exterior surface of a microvalve assembly 8 of the type in U.S. Pat. No. 4,474,889. The microvalve assembly 8 is a sandwich of silicon (about 12 mils thick), pyrex and polymer layers (not shown). The two exterior layers including top layer 10 are Pyrex about 50 mils thick. The gold and nickel traces are deposited on the surface of Pyrex layer 10 using conventional techniques of photolithography and deposition of metal films (e.g. metal sputtering). The heater element is the wide loop trace 11, and the temperature sensor is the narrow loop trace 12; both are of nickel.

Also shown are gold electrical contact pads 13, 14, 15, 17, 18, and a gold trace 22 which conducts electrical current to the end of the sample inlet tube which is bonded to the microvalve assembly at pad 17. Both the heater and sensor traces 11, 12 are formed by first a deposition of chromium about 50 Å thick on Pyrex 10, followed by an overlayer of nickel about 7,500 Å thick. The heater trace 11 is about 42 mils wide and the sensor trace 12 about 5 mils wide. Thus the sensor and heater traces in this example have resistances of about 400 ohms and about 20 ohms respectively. The resistances of the heater trace and the sensor trace are determined primarily by the cross-sectional area (thickness and width) of the trace and the overall length of the trace. The gold trace 22 and contact pads 13, 14, 15, 17, and 18 are about 1.2 µm thick similarly formed over 50 Å of chromium. Gold electrical contact pads 18 are provided for electrical connection to the nickel wire temperature sensor (see FIG. 2) which senses the temperature of the sample inlet tube. An eight-pin socket electrical connector (not shown) is bonded to the gold electrical contact pads 13, 14, 15, 16, 17, and 18, and the gold trace 22 in the fully-assembled microvalve assembly. The small crosses, e.g. 20, define locations of vias for passage of gas to the valve channels (not shown). (It is understood that all dimensions herein are exemplary.)

Figure 2:
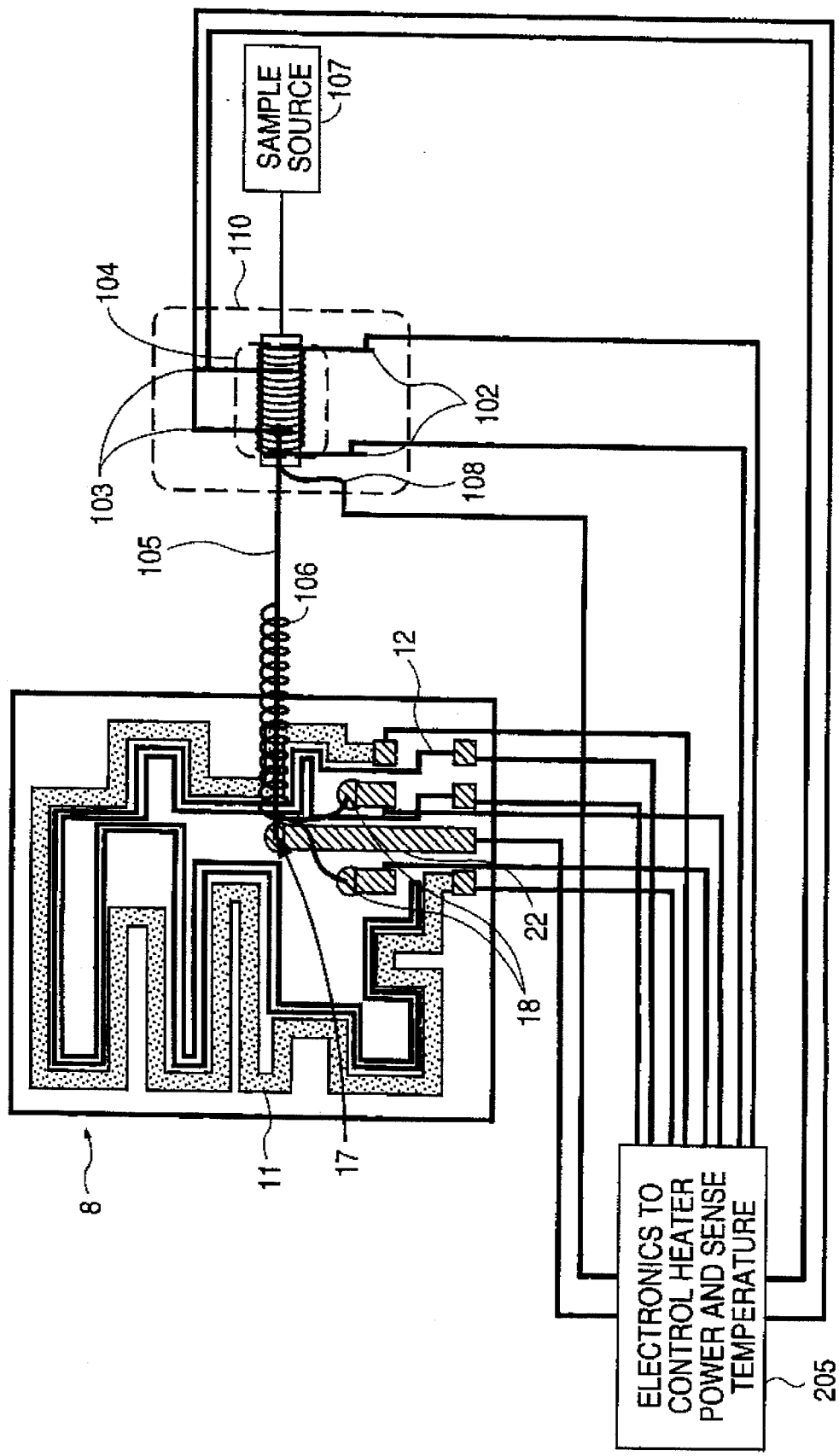
FIG. 2 is a diagram of heated zones including that of FIG. 1 showing the temperature sensor and heater of three heated zones which are the sample inlet fitting, sample inlet tube, and microvalve assembly.

FIG. 2 shows a diagram of three heated zones of an embodiment of the present invention: the three zones are the sample inlet fitting assembly 110, the sample inlet tube 105, and the microvalve assembly 8 of FIG. 1. The sample source 107 which is external to the gas chromatograph, is conventionally connected to the gas chromatograph at the sample inlet fitting 110, which lies within the windings 104 of the temperature sensor wire and the heater wire associated with the sample inlet fitting subassembly 110. The heater wire is nickel alloy-90 (12% nickel, 88% copper) wire about 3 mil in diameter having high-temperature electrical insulation (a coating of polyimide) with an electrical resistance of about 9 ohms per foot at room temperature. The sensor wire is pure nickel wire about 1 mil in diameter with an electrical resistance of about 45 ohms per foot at room temperature and similar electrical insulation.

The heater and sensor wires together form windings 104 on a metal sheath which fits over the sample inlet fitting in the sample inlet fitting assembly. The windings are held in place using high temperature epoxy. The terminal ends 103 of the sample inlet fitting temperature sensor wire, the terminal ends 102 of the sample inlet fitting heater wire, and a lead wire 108 to the sample inlet tube heater, join at an electrical connector (not shown) incorporated in the sample inlet fitting assembly 110.

The sample inlet tube (which incorporates a tube heater) 105 is either a single metal tube which conducts sample from the sample inlet fitting to the microvalve assembly 8, and is also the heater element; or alternatively is a pair of concentric tubes consisting of an outer metal tube (or a metal deposition on an inner tube) which is the heater element, and an inner tube (e.g. of fused silica) which carries the sample.

Figure 6:
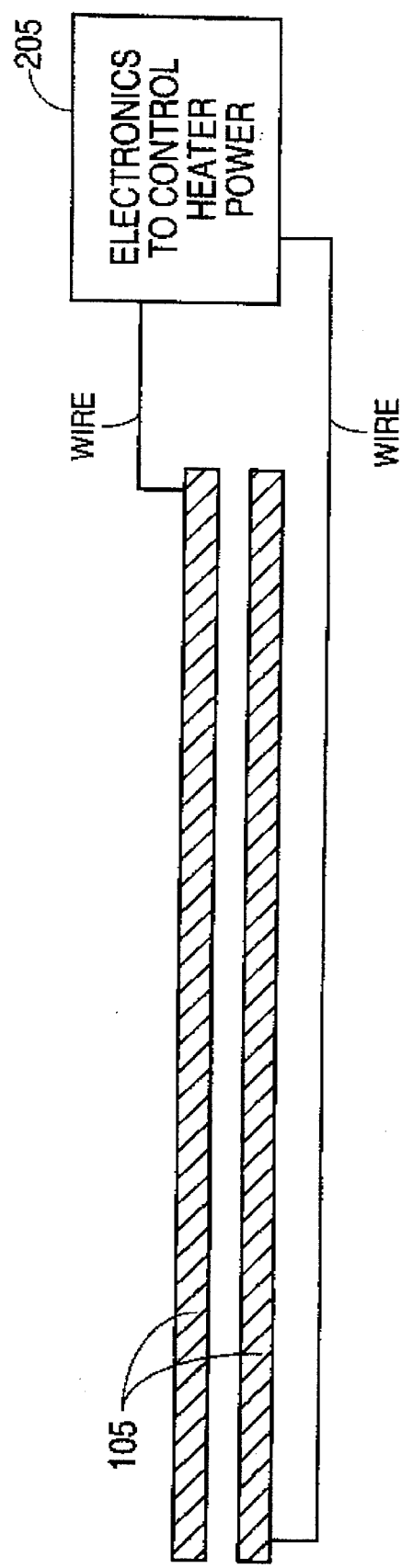
FIG. 6 shows a cross-section of the inlet tube.

The sample inlet tube 105 as shown in cross-section in FIG. 6 in one embodiment is formed of Inconel-625 (an alloy of about 62% nickel, 22% chromium, 9% molybdenum and several other elements) having a wall thickness of about 2 mil and an O. D. of about 20 mil. The sample inlet tube (or the heater portion thereof) 105 is electrically connected at pad 17 to trace 22 on the microvalve assembly 8. Electrical connections ("wire") to tube 105 are shown in FIG. 6. A jumper wire is soldered to pad 17 or trace 22, and also soldered to the sample inlet tube. The jumper wire is soldered to a gold band (¼" band, 50 microinches thick) electroplated on the sample inlet tube. The temperature sensor 106 for the sample inlet tube is wire wrapped around part of the sample inlet tube 105. The sample inlet tube temperature sensor wire 106 is electrically connected to electrical contact pads 18 on the microvalve assembly 8. Jumper wires are soldered to pads 18, and the temperature sensor wires are electrical-resistance welded to the jumper wires. Electrical power to the sample inlet tube (or the heater portion thereof) 105 flows through the electrical connector in the sample inlet fitting assembly 110, through the sample inlet tube heater, and through trace 22 to the eight-pin socket electrical connector in the microvalve assembly 8 via trace 22. One alternative to the eight-pin socket is connecting the wires which link to heated-zone electronics directly to the pad and sensor wire. All electrical connections connect to the electronics 205 to control heater power and sense temperature of each heated-zone, as also shown in FIG. 3.

For purposes of fabrication, the sensor wires and heater wires are electrical-resistance welded to the connector terminals (since nickel does not solder well); in the electrical-resistance welding process the high-temperature wire insulation is burned off at the electrical-resistance welds. The eight pin electrical connector is conventionally soldered to the appropriate gold contacts on the microvalve 8. The tubes connected to the microvalve assembly can be bonded to the assembly using adhesives which can tolerate high-temperatures, form gas-tight bonds, and are chemically-inert relative to the application of the microvalve assembly. Alternatively, these gas carrying tubes are first gold plated at their tips and then soldered to the gold contact areas on the micro-valve 8. Other methods for securing the tubes to the microvalve assembly are possible, such as compression-type fittings and o-rings.

Figure 3:
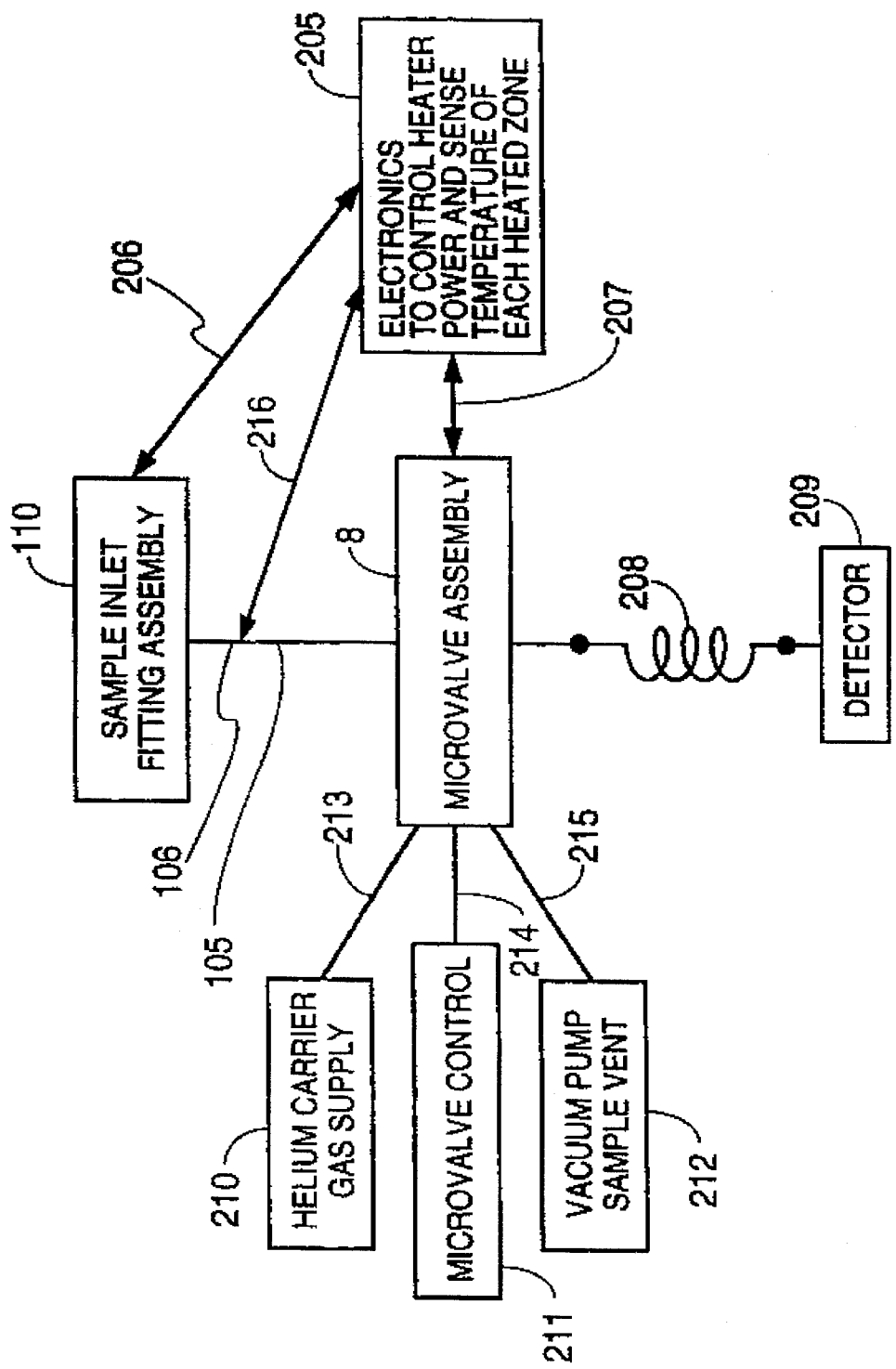
FIG. 3 is a schematic diagram of a miniature gas chromatograph system in an embodiment of the present invention.

FIG. 3 shows a schematic view of a gas chromatograph system in one embodiment of the present invention (this description includes elements shown in FIGS. 1 and 2 but described here in the context of the entire system). The sample inlet fitting is heated by passing electrical current through the heater wire incorporated in the sample inlet fitting assembly 110. The resistance of the second wire in the sample inlet fitting assembly 110 is sensed to monitor the temperature of the sample inlet fitting. An electrical connection to the sample inlet tube heater 105 is made at the sample inlet fitting assembly 110. The other electrical connection to the sample inlet tube heater 105 (to allow flow of electrical current through the tube heater 105) is made at the microvalve assembly 8.

The sample inlet tube/tube heater temperature sensor wire 106 is wrapped around a length of the sample inlet tube heater 105 near the microvalve assembly 8. The resistance of this wrapped nickel wire 106 is sensed to monitor the temperature of the sample inlet tube/tube heater 105. Electrical connection to the sample inlet tube/tube heater temperature sensor wire 106 is made at the microvalve assembly 8.

For heating of the microvalve assembly 8, there is provided the resistive heater trace on the surface of the assembly 8 through which the electrical current to heat the microvalve assembly 8 is passed. The resistance of the second trace on the surface of the assembly 8 is sensed to monitor the temperature of the microvalve assembly 8. Electrical connection to the temperature sensor and heater traces for the microvalve assembly 8 is made through a multipin connector attached to the electrical contact pads on the microvalve assembly 8.

Thermal insulation is incorporated in each heated zone. The metal sample inlet fitting is surrounded by a trapped-air space (about a 1 inch diameter, 1 inch long cylindrical space) in the sample inlet fitting assembly 110 which provides thermal insulation for the sample inlet fitting. The sample inlet tube/tube heater 105 is sheathed in fiberglass-reinforced silicone tubing or an outer layer of polyimide foam which provides thermal insulation for the sample inlet tube/tube heater 105. The microvalve assembly 8 is embedded in a thermally-insulating silicone rubber composite material and polyimide foam.

Figures 4A, 4B:
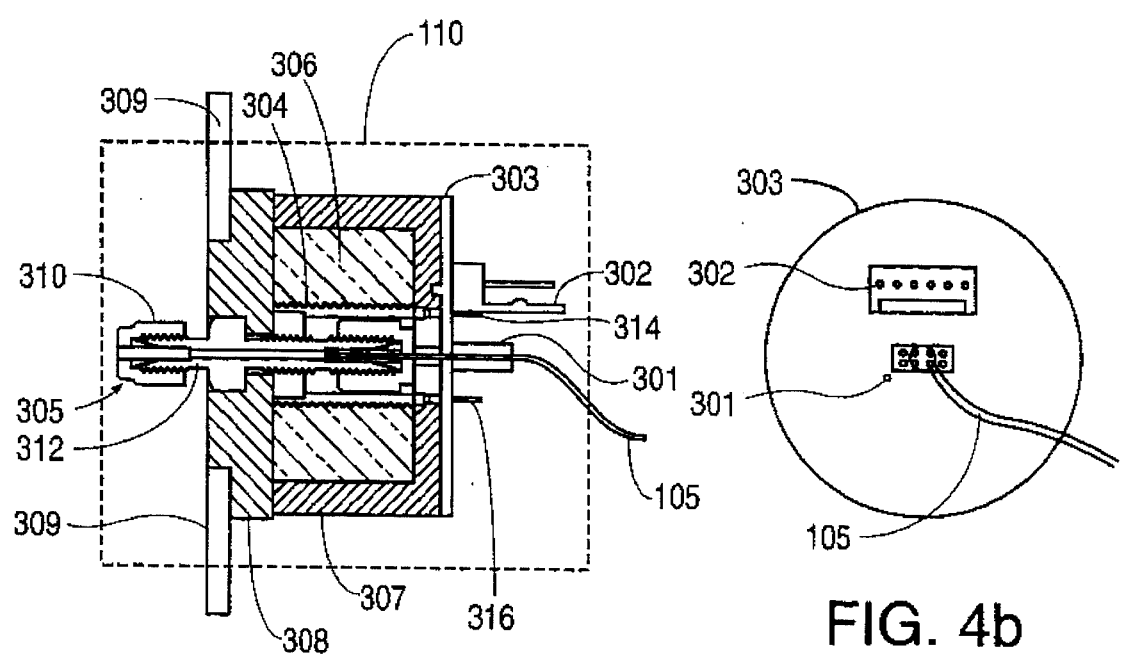
FIGS. 4a and 4b are diagrams of the sample inlet fitting assembly, including the printed circuit board which makes electrical connections to the sample inlet tube heater, and the inlet fitting heater and temperature sensor.

FIGS. 4a, 4b are a more detailed diagram of the sample inlet fitting assembly 110. FIG. 4a is a cross-section of the sample inlet fitting assembly 110 and FIG. 4b is a top view of the inlet PCB 303. The heater wire and temperature sensor wire windings 104 are wrapped around a metal inlet heater core 304 (aluminum or copper) having electrical contacts 314, 316 and which slips over one end of the sample inlet fitting 305 (which is a stainless steel ¹/₁₆" Swagelok bulkhead union). Externally threaded fitting 305a fits inside sample inlet fitting 305 and holds inlet tube 105. The inlet heater housing 307 fits onto the inlet block 308, which is fastened to the chromatograph instrument front panel 309. The sample inlet fitting 305 is fastened to the inlet block 308. The heater wire terminal ends 102 and the temperature sensor wire terminal ends 103 are electrically-connected to the inlet PCB 303. These wires ends 102 and 103 can be electrical-resistance welded to wires or pins attached to traces in the inlet PCB 303. The inlet PCB 303 is fastened to the inlet heater housing 307. The thermal insulation 306 inside the sample inlet fitting assembly is a trapped-air space. Electrical connection to the sample inlet tube heater 105 is made via an 8-element TEKA connector 301. The sample inlet tube 105 passes through one of the sites in the TEKA connector 301 and through a hole in the inlet PCB 303, and is secured in one end of the sample inlet fitting 305 using a nut 310 and ferrule 312. Several sample inlet tubes 105 can be accommodated, each using one of the several sites in the TEKA connector 301, and each feeding into a hole in a multi-hole ferrule. Electrical connection of the sample inlet fitting assembly 110 to the heated-zone electronics is made via a cable 206 which attaches to electrical connector 302.

Electronics 205 in FIG. 3 are provided to measure the electrical resistance (varying with temperature) of the temperature sensors in the heated zones, and provide an appropriate amount of electrical current to maintain the set temperature (in one embodiment 110° C.).

Figure 5A:
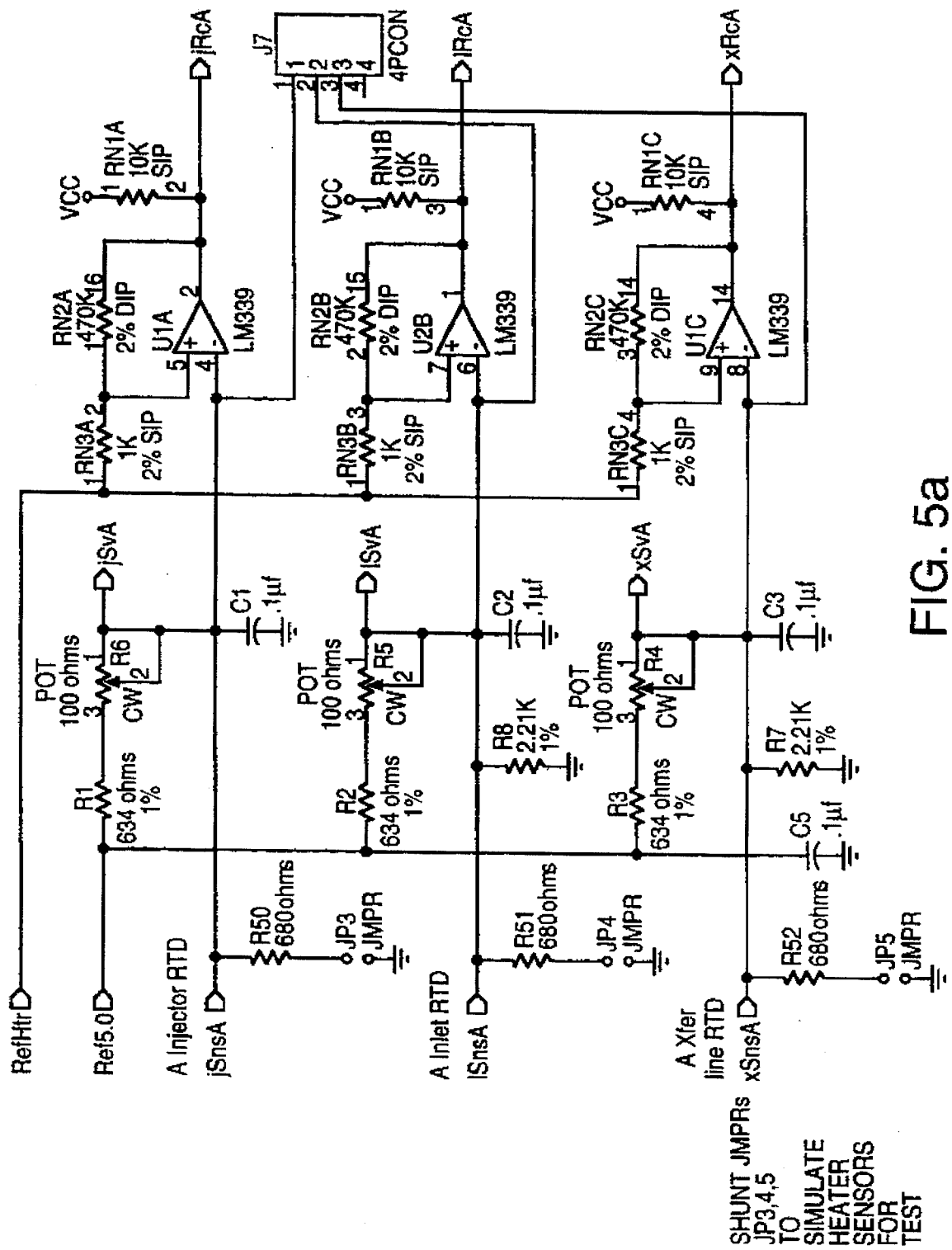
FIGS. 5a to 5g are schematic diagrams of the heater control circuitry.
Figure 5B:
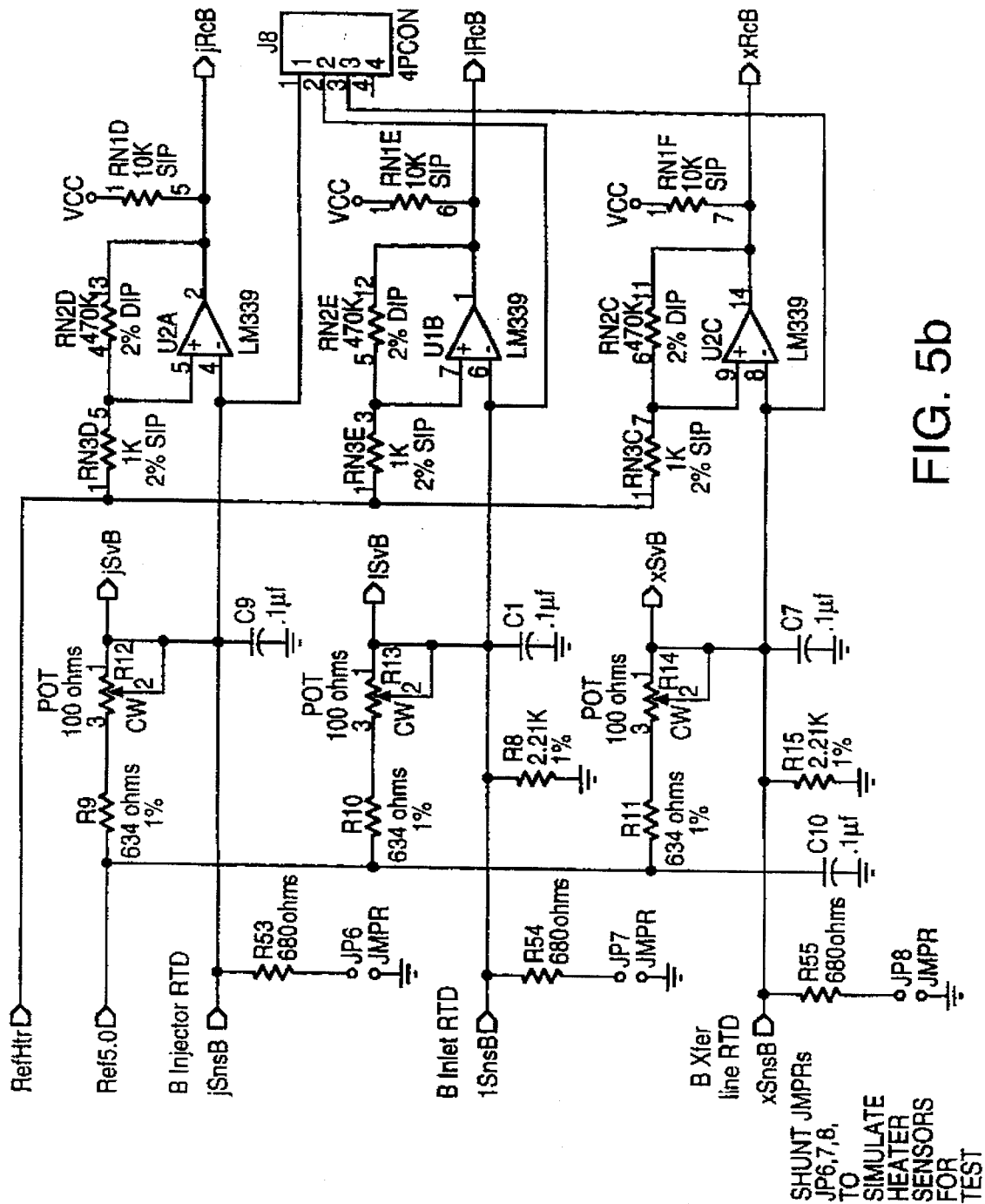

The heated-zone control circuitry represented schematically in FIGS. 5a to 5g controls two sets of heated zones. FIGS. 5a and 5b show the temperature sensing circuits for a set of heated zones consisting of one microvalve heater (Injector), one sample inlet (Inlet) and one sample inlet tube (Xfer Line). In operation (e.g. the Channel A microvalve heater, labelled "A Injector RTD" FIG. 5a), a reference sensor voltage (Ref 5.0) is applied across the temperature sensor (e.g. jSnsA) through a voltage divider.

The voltage is distributed between the temperature sensor and the voltage divider according to the temperature-dependent resistance of the temperature sensor and the resistance of a resistor which is chosen to establish the heated-zone set temperature (e.g. R6). The distributed-voltage is compared to another reference voltage (RefHtr) at the input of a analog comparator (e.g. U1A). When the difference between the two voltages exceeds a certain value, the output of the analog comparator toggles between TTL low and TTL high. This toggled TTL signal is directed to a Programmable Array Logic device (shown in FIG. 5f as U10), which acts to sequence the powering of all the heaters so that only one heater is powered at any time.

An inductor in the output to each heater minimizes noise and cross-talk arising from the switching of power to the heaters. The injector heater (microvalve assembly) and the sample inlet fitting heater are switched to ground. The sample inlet tube (Xfer Line) is switched to power and is grounded at the sample inlet fitting, to prevent short circuiting between the gas chromatograph and tubing connected externally at the sample inlet fitting.

Figure 5C:
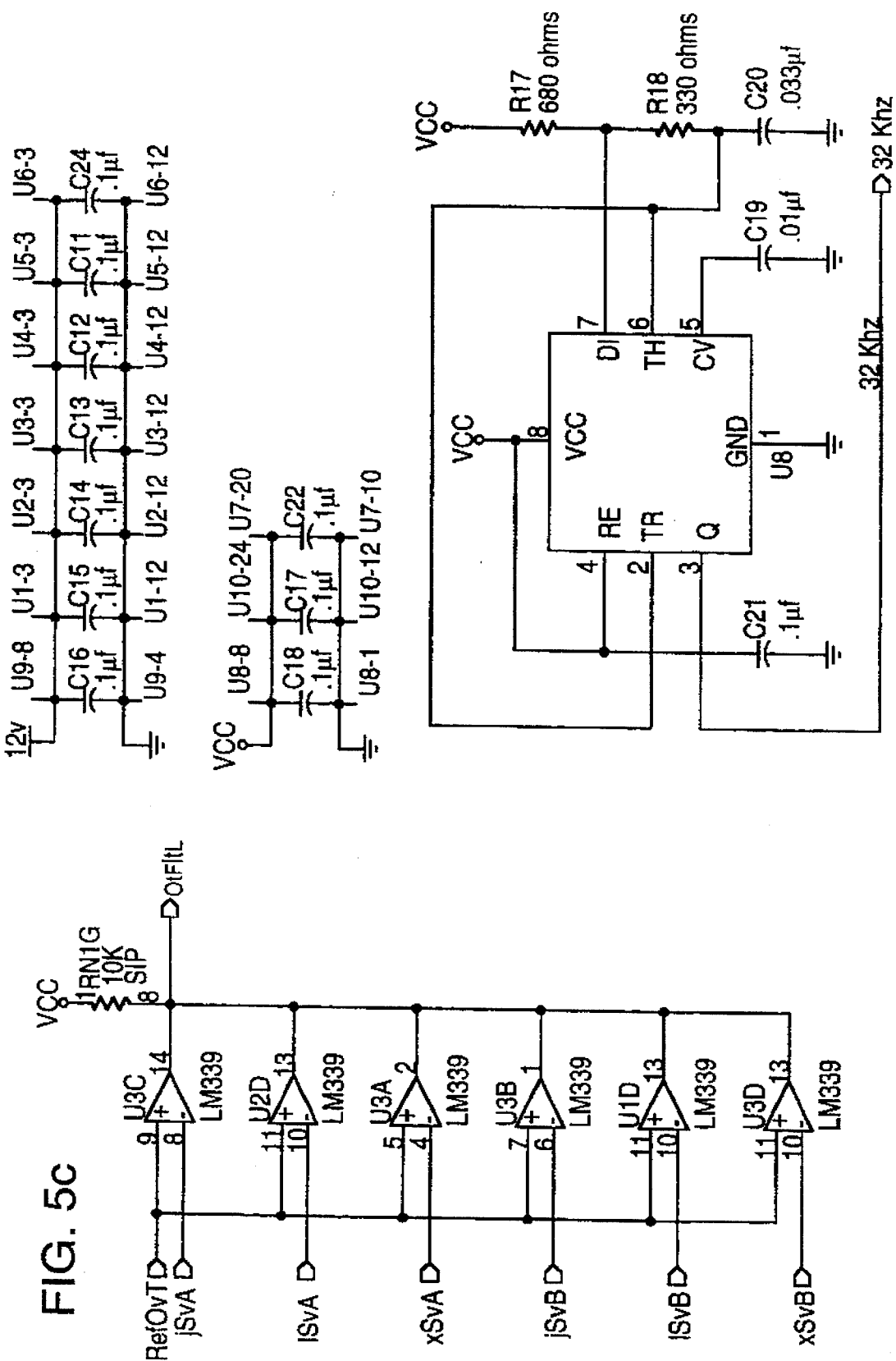
Figure 5D:
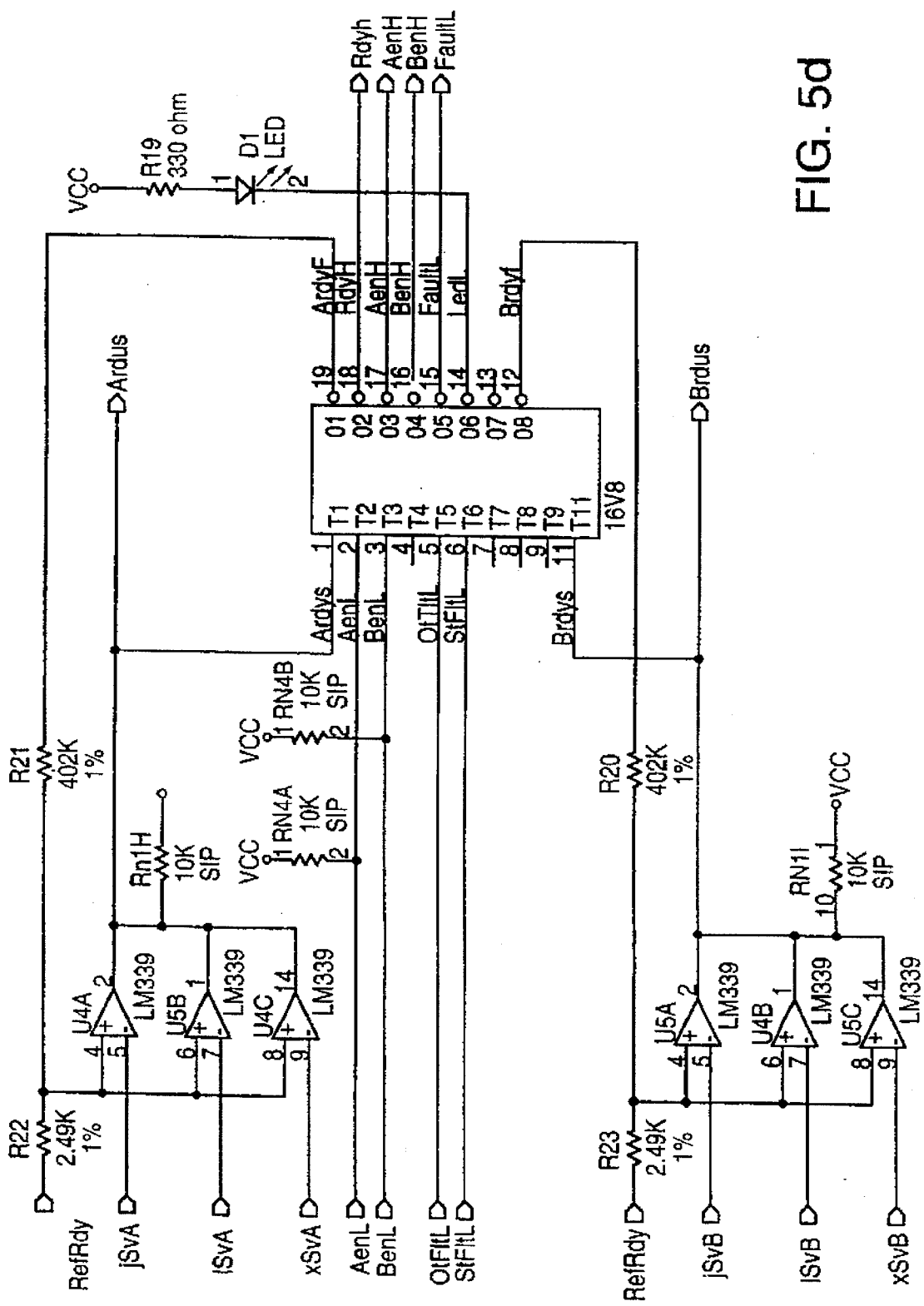

In order to detect an overtemperature condition of a heated zone, protection circuitry is provided as shown in FIG. 5c. For each heated zone, a voltage from the temperature sensor voltage divider (e.g. jSvA) is compared to an overtemperature reference voltage (RefOvT) at the input of a analog comparator (e.g. U3C). When the difference between these two voltages exceeds a certain value, the analog comparator output toggles between TTL low and TTL high. This toggles the value of OtFltL, which is an input to another Programmable Array Logic device (U7), which communicates to the host gas chromatograph electronics and controls the overall operation of the heated-zone circuitry.

Figure 5E:
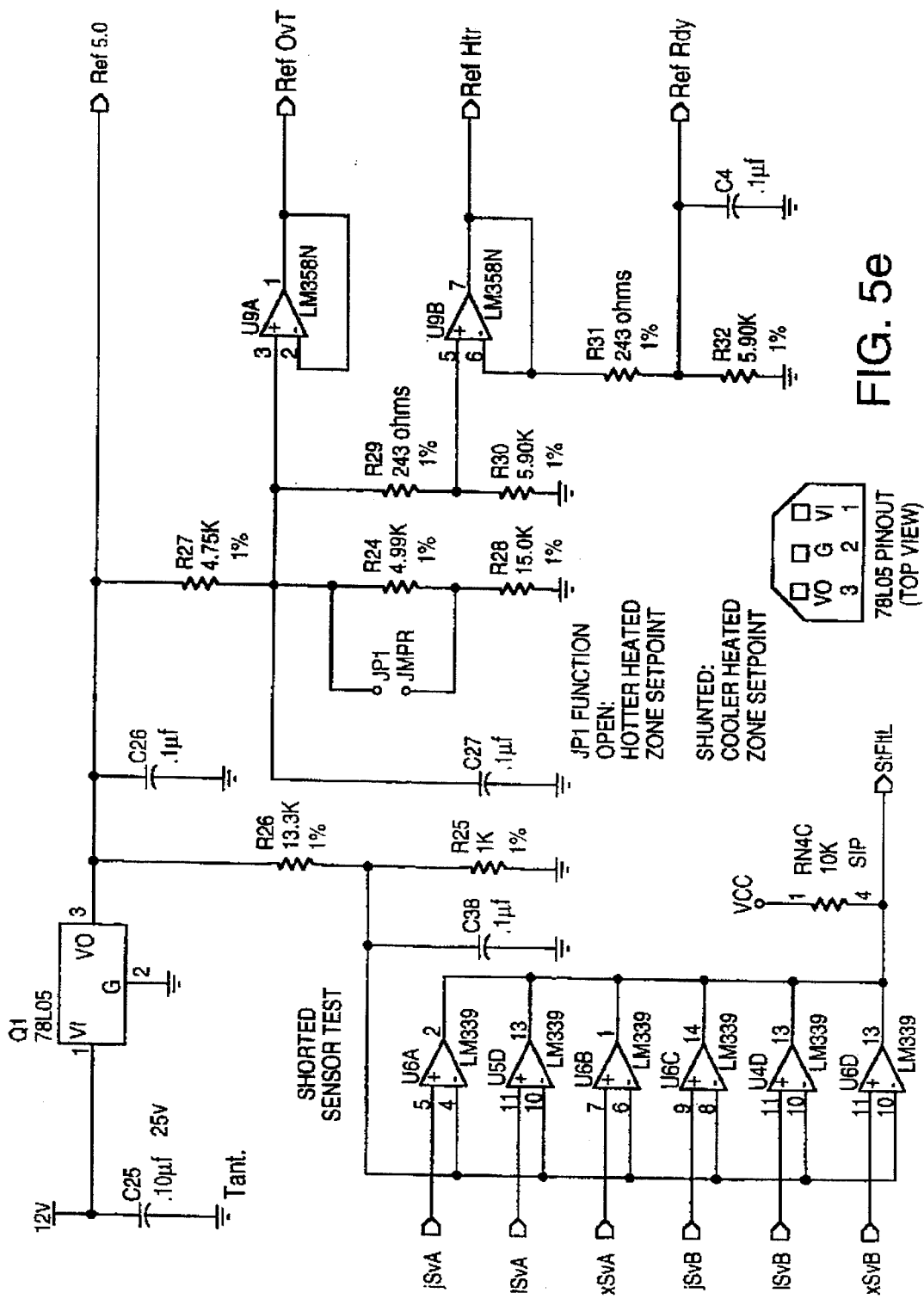
Figure 5F:
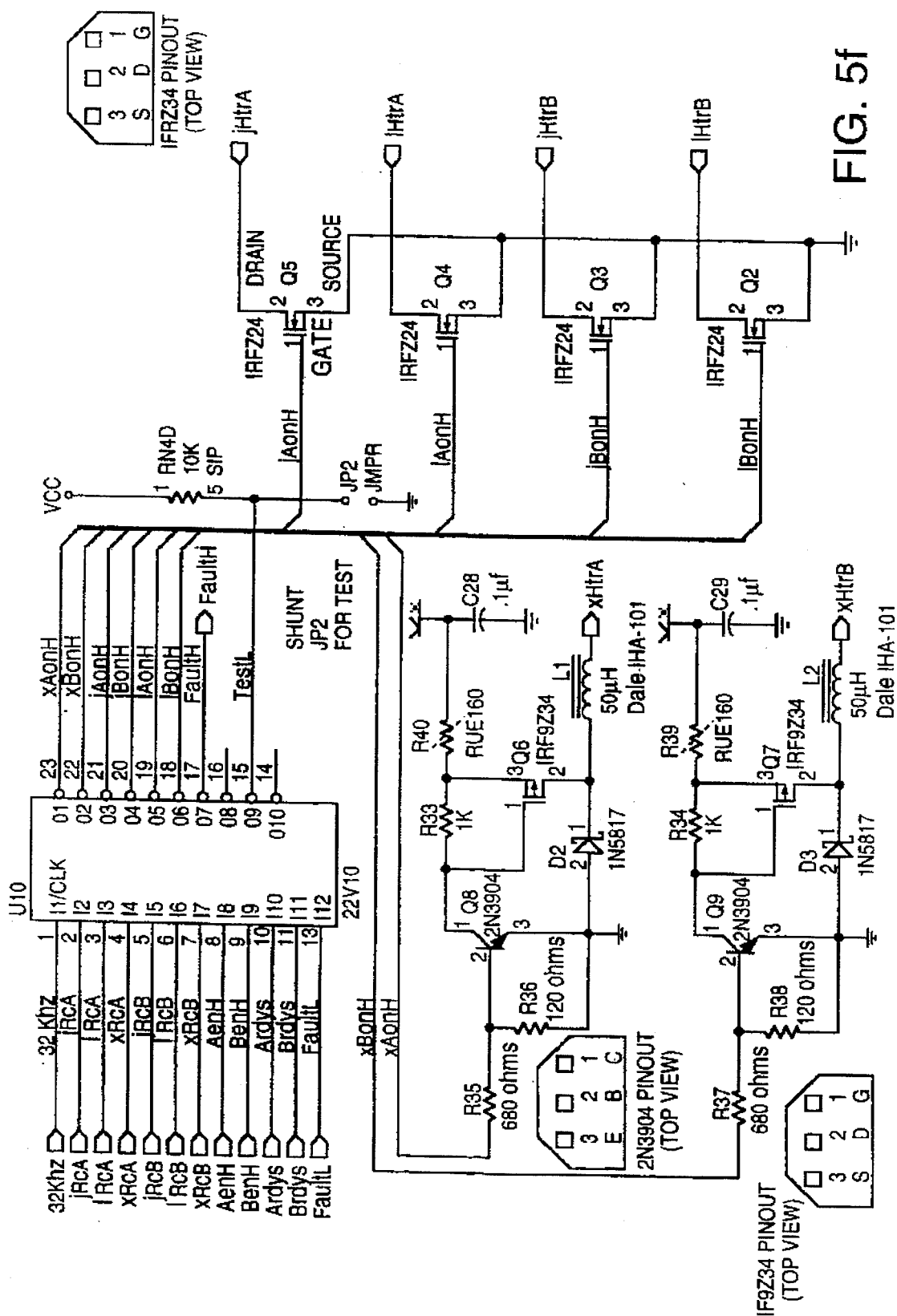
Figures 1, 5G:
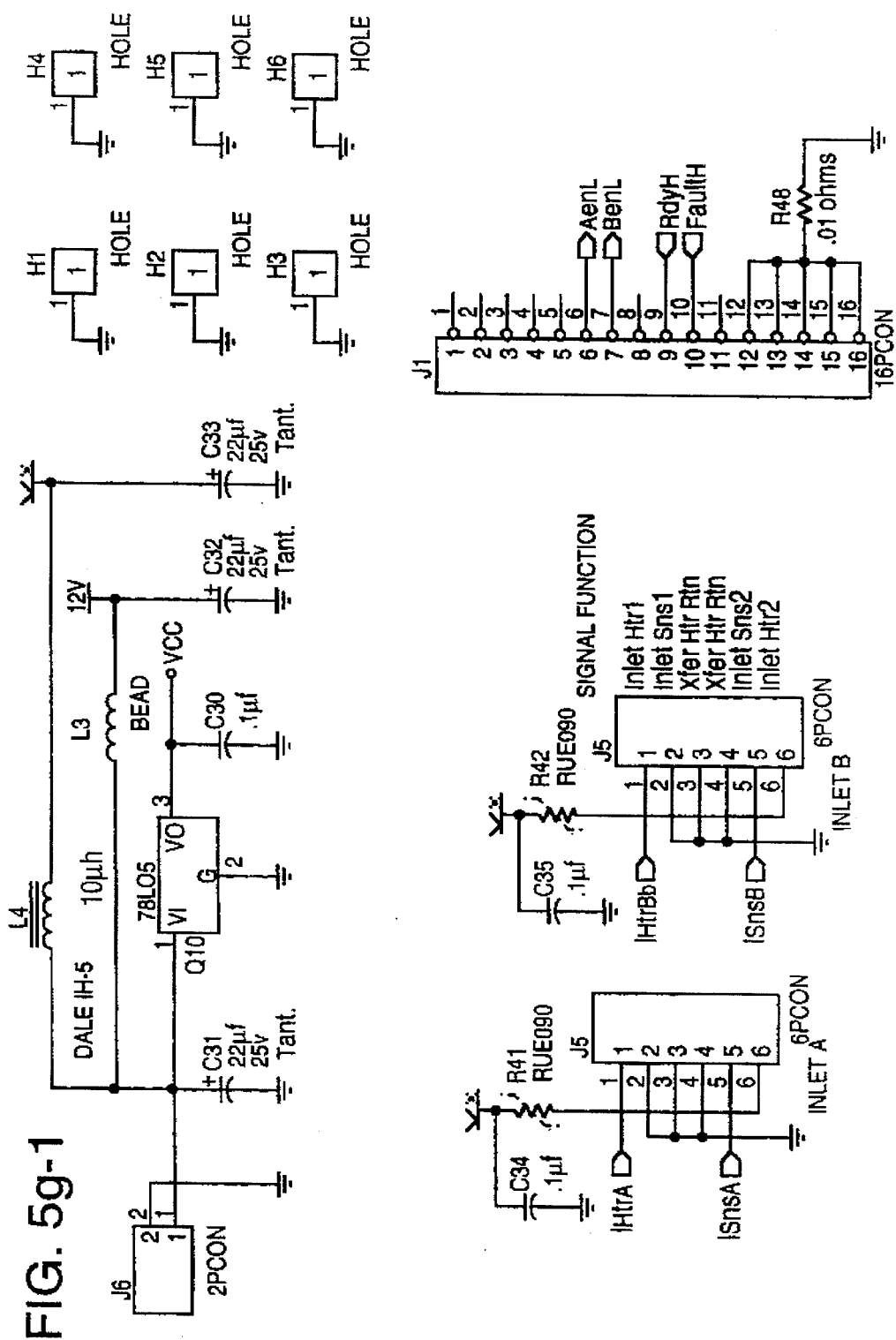
Figures 2, 5G:
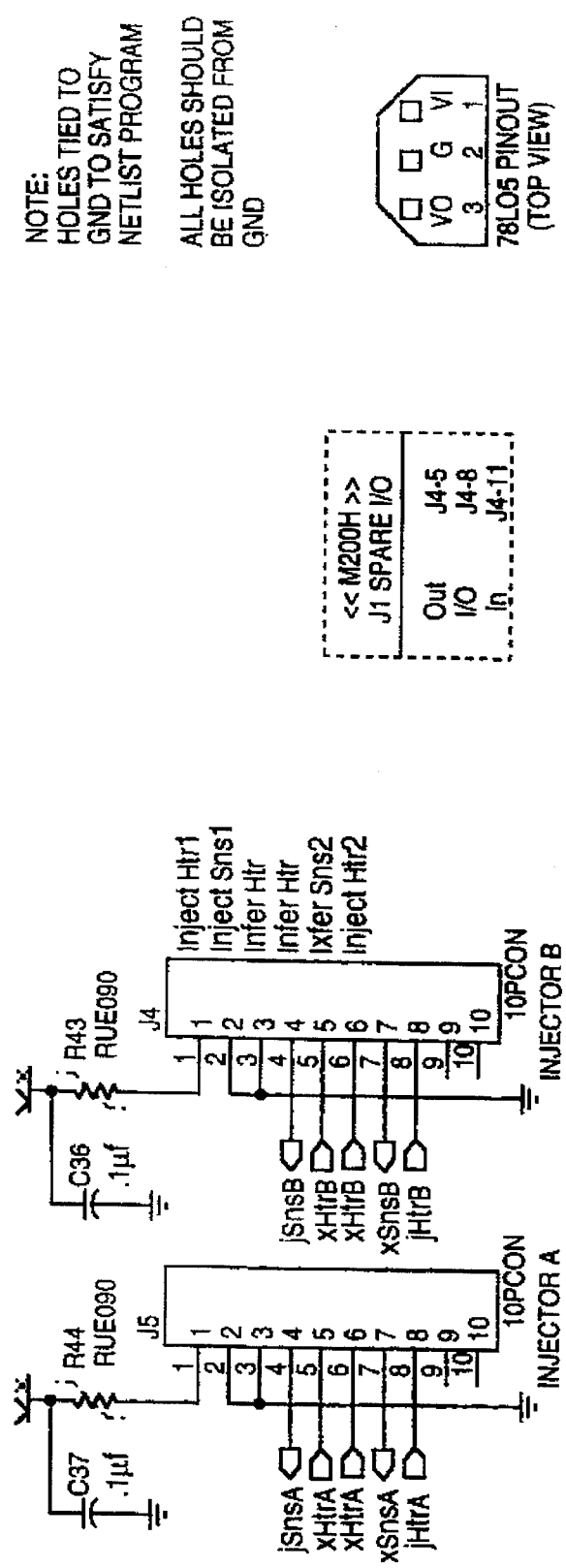

When the value of OtFltL toggles, indicating an overtemperature condition, the heating of the heated zones is suspended. Circuitry to detect a shorted temperature sensor is also provided, which is shown in FIG. 5e and operates similar to the overtemperature circuitry, and communicates to the control Programmable Array Logic device (U7) through signal StFltL. The connectors which link the circuitry to the heaters, temperature sensors and the host gas chromatograph electronics are shown in FIG. 5g. Connector J1 connects to the host gas chromatograph electronics. Connector J3, for example, connects to one of the sample inlets (Inlet A), and provides the ground connection for the sample inlet tube (Xfer Line), in addition to the connections to the inlet heater and inlet temperature sensor. Connector J5, for example, connects to one of the microvalve assemblies (Injector A), providing power to the microvalve assembly heater and the sample inlet tube (Xfer Line A), and connects to the temperature sensors for those two heated zones.

The heated zones can be controlled by less sophisticated, conventional circuitry in the alternative.

The electronics 205 communicates with the sample inlet fitting assembly 110 through an electrical cable 206. The electronics 205 communicates with the microvalve assembly 8 through an electrical cable 207. The electronics 205 communicates with the inlet tube 105 and its temperature sensor 106 through an electrical cable 216. Carrier gas supply 210 is provided to the microvalve assembly 8 through a tube 213. A control 211 for the microvalves is provided, which communicates with the microvalve assembly through a means 214.

For example, in one embodiment, the microvalves are diaphragm valves. The valve diaphragm is a flexible sheet of Kapton (a Dupont product). The valve diaphragm is pressed against the valve seat using a pressurized gas, thereby closing the valve. The valve opens when the gas pressure is released. The pressurized gas is conducted to the valve diaphragm via tubes 214 which connect each microvalve in the microvalve assembly to a solenoid valve which is external to the microvalve assembly. The control 211 is the solenoid valve, which toggles between two states: one state sends pressurized gas to the valve diaphragm, thereby closing the valve; the other state releases the gas pressure, thereby opening the valve. In another embodiment, the microvalves are electrically actuated by electrical elements which are incorporated in the microvalve assembly, and wires 214 communicate the control signals from a control 211 to the microvalve assembly.

A vacuum pump or vent 212 to draw the sample is provided, which draws a sample from the microvalve assembly 8 through a tube 215. Alternatively, the sample flows under pressure through the microvalve assembly to the vent 212. A conventional analytical column 208 physically separates the components of the sample. A conventional detector 209 senses the presence of components in the sample as the components exit the analytical column.

The power supply for the three heater elements in one embodiment is from a 12 volt battery; in another embodiment, a mains power source of about 12 VDC is the power supply. The heater control circuit provides the appropriate amount of electrical power to each heated-zone heater to maintain the set temperature as sensed using the temperature sensor for the heated zone. Each heated zone can be such that the heater can be powered by 12 VDC; however, the heater control circuit can provide electrical power at another voltage or frequency, as appropriate.

Other tubes communicating fluids to the microvalve can be heated in a manner similar to the sample inlet tube. For example, it may be desirable to heat the tube connecting the microvalve assembly to the vacuum pump or vent 212.

In the above described embodiments, each of three heated zones is temperature controlled to the same predetermined temperature; in another embodiment the predetermined temperatures may differ. Also, in another embodiment the inlet fitting is not temperature controlled.

In yet another embodiment, the heater and sensor traces instead of being formed directly on the micro-valve surface are formed on a thin film (e.g. Kapton) and then the thin film is adhered to the Pyrex surface of the microvalve assembly, thereby achieving good thermal contact to the microvalve assembly, energy-efficient heating, and a low thermal mass for the heater and sensor. Alternatively, a heater wire and sensor wire (similar to that usable for the sample inlet fitting described above) can be connected to the microvalve assembly with adhesive or tape.

The heating technique disclosed herein is usable in combination with the fixed-volume micro-valve injector disclosed in copending and commonly owned U.S. Pat. No. 5,487,313 issued on Jan. 31, 1996, entitled "Fluid-Lock Fixed-Volume Injector" invented by Paul H. Johnson, incorporated herein by reference, as well as with the microvalve of above-referenced U.S. Pat. No. 4,474,889.

The description herein is illustrative and not limiting; further modifications will be apparent to one skilled in the art.

We claim:

1. A microvalve assembly comprising:
    a body defining a plurality of channels interconnected by valves formed in the body;
    a tube connected at one end to the body;
    a fitting for connection of the tube to a fluid source or sink and located at the other end of the tube;
    three heater elements, one of the elements being respectively in thermal contact with each of the body, the tube, and the fitting; and
    a control circuit connected to the heater elements for controlling each of the heater elements.

2. A microvalve assembly comprising:
    a body defining a plurality of channels interconnected by valves formed in the body;
    a tube connected at one end to the body;
    a fitting for connection of the tube to a fluid source or sink and located at the other end of the tube;
    three heater elements, one of the elements being respectively in direct thermal contact with each of the body, the tube, and the fitting; and
    a control circuit for controlling a supply of electrical current to each of the heater elements.

3. The microvalve assembly of claim 2, further comprising three temperature sensing elements, one of the three elements being respectively in direct thermal contact with each of the body, the tube, and the fitting.

4. The microvalve assembly of claim 3, wherein the body includes a plurality of layers, and the heater element and temperature sensing element in contact with the body are each electrically conductive traces formed on a surface of at least one of the layers.

5. The microvalve assembly of claim 4, wherein each trace is metal deposited on the surface of one of the layers.

6. The microvalve of claim 3, wherein the temperature sensing element in contact with the tube is an insulated conductor wrapped around the tube.

7. The microvalve of claim 3, wherein the temperature sensing element in contact with the fitting is an insulated conductor wrapped around the fitting.

8. The microvalve assembly of claim 2, wherein the tube has a wall thickness in a range of 1 to 3 mils.

9. The microvalve assembly of claim 2, wherein the tube is a single metal unlined metal tube connecting to one of the channels for providing a passage to the one of the channels, and further comprising electrical connections to the tube for passing an electric current through the tube.

10. A method of controllably heating a microvalve assembly which includes as elements a valve body, a tube connected at one end to the valve body, and a fitting for connection of the tube to a fluid source or sink and located at the other end of the tube, comprising the steps of:
    individually heating each of the valve body, the tube, and the fitting elements;
    sensing the temperature of each heated element individually; and
    controlling a supply of heating electrical current to each of the heated elements in response to the sensed temperature of that element.

* * * * *